(12) United States Patent
Kinnunen et al.

(10) Patent No.: US 11,986,313 B2
(45) Date of Patent: *May 21, 2024

(54) METHOD AND SYSTEM FOR MONITORING AND IMPROVING SLEEP PATTERN OF USER

(71) Applicant: Oura Health Oy, Oulu (FI)

(72) Inventors: Hannu Kinnunen, Oulu (FI); Heli Koskimäki, Oulu (FI); Harri Laakkonen, Oulu (FI); Mika Erkkilä, Oulu (FI)

(73) Assignee: Oura Health Oy, Oulu (FI)

( * ) Notice: Subject to any disclaimer, the term of this patent is extended or adjusted under 35 U.S.C. 154(b) by 2 days.

This patent is subject to a terminal disclaimer.

(21) Appl. No.: 17/971,424

(22) Filed: Oct. 21, 2022

(65) Prior Publication Data
US 2023/0040407 A1 Feb. 9, 2023

Related U.S. Application Data

(63) Continuation of application No. 16/767,440, filed as application No. PCT/FI2018/050848 on Nov. 21, 2018, now Pat. No. 11,478,187.

(30) Foreign Application Priority Data

Nov. 29, 2017 (FI) ...................................... 20176070
Apr. 30, 2018 (FI) ...................................... 20185398

(51) Int. Cl.
*A61B 5/00* (2006.01)
*A61B 5/0205* (2006.01)
(Continued)

(52) U.S. Cl.
CPC .......... *A61B 5/4815* (2013.01); *A61B 5/0002* (2013.01); *A61B 5/02055* (2013.01);
(Continued)

(58) Field of Classification Search
CPC ... A61B 5/4815; A61B 5/0002; A61B 5/1118; A61B 5/4809; A61B 5/486; A61B 5/6801
See application file for complete search history.

(56) References Cited

U.S. PATENT DOCUMENTS

2011/0267196 A1 11/2011 Hu et al.
2016/0151603 A1 6/2016 Shouldice et al.
(Continued)

OTHER PUBLICATIONS

Finnish Patent and Registration Office, Search Report, Patent Application No. 20185398, dated Aug. 20, 2018.

*Primary Examiner* — Lynsey C Eiseman
*Assistant Examiner* — Naveed R. Kolia
(74) *Attorney, Agent, or Firm* — Holland & Hart LLP

(57) ABSTRACT

A method and a system for providing feedback to a user for adjusting sleep pattern of the user. The method includes collecting a set of information related to the user, receiving a set of measurement data related to the user from a wearable electronic device, defining circadian rhythm and duration of sleep of the user, determining sleep scores for a predefined number of days and associating each sleep score with a corresponding go-to-bed time or time of falling asleep of the user. A sleep score is determined for each of the predefined number of days from the collected set of information, the set of measurement data, the circadian rhythm and the duration of sleep of the user. The method further includes analysing the sleep scores and associated go-to-bed time or time of falling asleep of the user to determine an optimum bedtime window for the user and providing feedback to the user based on the analysed sleep scores and the optimum bedtime window.

20 Claims, 7 Drawing Sheets

(51) Int. Cl.
*A61B 5/024* (2006.01)
*A61B 5/11* (2006.01)
*G16H 20/30* (2018.01)

(52) U.S. Cl.
CPC .......... *A61B 5/1118* (2013.01); *A61B 5/4809* (2013.01); *A61B 5/486* (2013.01); *A61B 5/6801* (2013.01); *G16H 20/30* (2018.01); *A61B 5/02438* (2013.01); *A61B 2562/0219* (2013.01); *A61B 2562/0271* (2013.01)

(56) References Cited

U.S. PATENT DOCUMENTS

| | | |
|---|---|---|
| 2016/0270717 A1 | 9/2016 | Luna et al. |
| 2016/0361515 A1 | 12/2016 | Jung et al. |
| 2017/0055899 A1 | 3/2017 | Bandyopadhyay et al. |
| 2017/0132946 A1 | 5/2017 | Kinnunen et al. |
| 2017/0135632 A1 | 5/2017 | Franceschetti et al. |
| 2018/0042540 A1* | 2/2018 | Kinnunen .......... A61B 5/02433 |

* cited by examiner

METHOD AND SYSTEM FOR MONITORING AND IMPROVING SLEEP PATTERN OF USER

CROSS REFERENCE

The present Application for Patent is a continuation of U.S. patent application Ser. No. 16/767,440 by KINNUNEN, et al., entitled "METHOD AND SYSTEM FOR MONITORING AND IMPROVING SLEEP PATTERN OF USER", filed May 27, 2020, assigned to the assignee hereof, and is expressly incorporated by reference in its entirety herein.

TECHNICAL FIELD

The present disclosure relates generally to analysis and processing of data related to sleep pattern of a user; and specifically, to methods and systems for providing feedback to a user for improving sleep pattern thereof. More specifically, the present disclosure relates to improving overall sleep quality and sleep score of the user by guiding the user to find an optimal bedtime.

BACKGROUND

Though modernization has made lives global and easier, it has lead individuals to adopt harmful and adverse life styles. For example, individuals may have irregular timings at work owing, increased screen time caused by higher usage of devices such as mobile, computer and so forth, extended work load leading to higher stress levels, frequent travelling and so forth. Furthermore, frequent travelling may also cause additional time zone adaptation issues for individuals. Consequently, such harmful and adverse life style may have unfavourable impact on health and chronotype of the individuals. Specifically, such life style may cause distorted sleep pattern and disrupted sleep.

Furthermore, distorted sleep pattern and disrupted sleep may lead to various problems like disturbance in circadian rhythm, insomnia, delayed sleep phase disorder, depression and so forth. Additionally, distorted sleep pattern may also cause health issues like high blood pressure, diabetes, heart failure and so forth. Specifically, individuals with such problems may feel drowsy all the time, thus causing safety risks. Furthermore, such a condition may highly affect productivity of the individuals by affecting ability to judge and memory thereof.

Conventionally, existing applications may help a user in improving sleep pattern thereof by providing optimal go-to-bed time and wake-up time. Such applications provide a strict schedule for optimal go-to-bed time and wake-up time. Consequently, such applications lead to stress around sleeping hours of the user and further causing disturbance in sleep. Furthermore, such applications are very stern (namely, firm, demanding) and do not consider physical health and activities carried out by the user. Therefore, use of such applications for providing optimal go-to-bed time and wake-up time may negatively affect daily routine as well as mental state of the user.

Document U.S. 2017/132946 discloses a device and method for providing feedback to a user, based on information and measurement data related to the user. The document does discuss sleep scores, but merely to follow up on how the sleep quality has been improved when the user has followed instructions given by the device. Indeed, in the method firstly the go-to-bed time is first defined (in different conditions such as time zone change or changing from winter time to summer time) and secondly following how it affects to the sleep score of the person. Therefore, in light of the foregoing discussion, there exists a need to overcome the aforementioned drawbacks of the existing applications for improving sleep pattern of the user.

SUMMARY

The present disclosure seeks to provide a method for providing feedback to a user for adjusting sleep pattern of the user. The present disclosure also seeks to provide a system for providing feedback to a user for adjusting sleep pattern of the user. The present disclosure seeks to provide a solution to the existing problem of disturbed sleep pattern of the user. An aim of the present disclosure is to provide a solution that overcomes at least partially the problems encountered in prior art, and provides adaptive, reliable and personalised sleep pattern for the user.

The present disclosure relates to improving the sleep pattern of user, wherein the sleep pattern of the user comprises bedtime of the user (namely, a go-to-bed time), time of falling asleep of the user, wake-up time, quality of sleep, activity during sleep, time of REM-phase, length of REM-phase, time of non-REM phase, length of non-REM phase and so forth. Furthermore, the present disclosure seeks to increase a duration of sleep of the user and also improve the quality of sleep thereof.

In one aspect, an embodiment of the present disclosure provides a method for providing feedback to a user for adjusting sleep pattern of the user, the method comprising:
  collecting a set of information related to the user;
  receiving a set of measurement data related to the user from a wearable electronic device;
  defining circadian rhythm and duration of sleep of the user;
  determining sleep scores for a predefined number of days, wherein a sleep score is determined for each of the predefined number of days from the collected set of information, the set of measurement data, the circadian rhythm and the duration of sleep of the user, and associating each sleep score with a corresponding go-to-bed time or time of falling asleep of the user;
  analysing the sleep scores and associated go-to-bed time and/or time of falling asleep of the user to determine an optimum bedtime window for the user; and
  providing feedback to the user based on the analysed sleep scores and the optimum bedtime window, wherein the feedback comprises instructions to the user related to adjusting the sleep pattern.

In another aspect, an embodiment of the present disclosure provides a system for providing feedback to a user for adjusting sleep pattern of the user, the system comprising:
  a wearable electronic device configured to be worn by the user and comprising means for measuring a set of measurement data;
  a mobile communication device configured to communicate with the wearable electronic device and operable to collect a set of information related to the user;
  wherein the mobile communication device or the wearable electronic device is operable to measure circadian rhythm and duration of sleep of the user; and
  a processing module configured to communicate with at least one of the mobile communication device and the wearable electronic device, the processing module operable to:

receive the set of measurement data related to the user from the wearable electronic device;

receive the set of information related to the user from the mobile communication device;

receive the measured circadian rhythm and duration of sleep of the user from the wearable electronic device or the mobile communication device;

determine sleep scores for a predefined number of days, wherein a sleep score is determined for each of the predefined number of days from the collected set of information, the set of measurement data, the circadian rhythm and the duration of sleep of the user, and associate each sleep score with a corresponding go-to-bed time or time of falling asleep of the user;

analyse the sleep scores and associated go-to-bed time or time of falling asleep of the user to determine an optimum bedtime window for the user; and provide feedback to the user on the mobile communication device, based on the analysed sleep scores and the optimum bedtime window, wherein the feedback comprises instructions to the user related to adjusting the sleep pattern.

Embodiments of the present disclosure substantially eliminate or at least partially address the aforementioned problems in the prior art, and enables a seamless, interactive and stress-free method of improving sleep pattern of a user.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
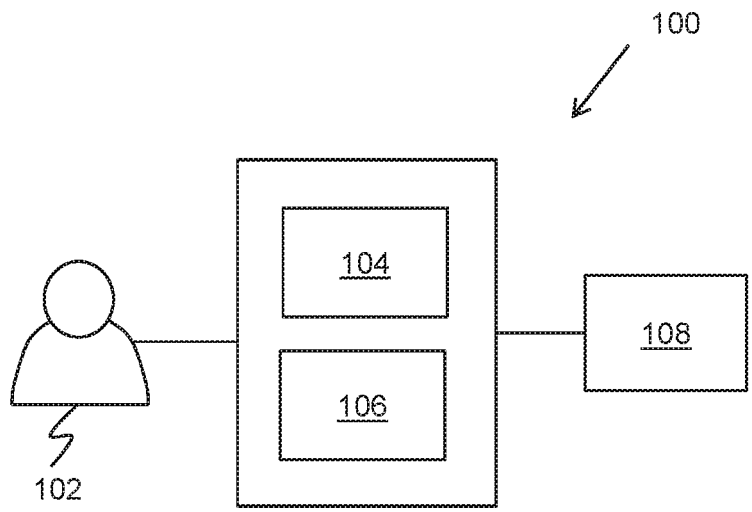
FIG. 1 is a schematic illustration of a system for providing feedback to a user for adjusting sleep pattern of the user, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method for providing feedback to a user for adjusting sleep pattern of the user, the method comprising:

collecting a set of information related to the user;

receiving a set of measurement data related to the user from a wearable electronic device;

defining circadian rhythm and duration of sleep of the user;

determining sleep scores for a predefined number of days, wherein a sleep score is determined for each of the predefined number of days from the collected set of information, the set of measurement data, the circadian rhythm and the duration of sleep of the user, and associating each sleep score with a corresponding go-to-bed time or time of falling asleep of the user;

analysing the sleep scores and associated go-to-bed time and/or time of falling asleep of the user to determine an optimum bedtime window for the user; and providing feedback to the user based on the analysed sleep scores and the optimum bedtime window, wherein the feedback comprises instructions to the user related to adjusting the sleep pattern.

In another aspect, an embodiment of the present disclosure provides a system for providing feedback to a user for adjusting sleep pattern of the user, the system comprising:

a wearable electronic device configured to be worn by the user and comprising means for measuring a set of measurement data;

a mobile communication device configured to communicate with the wearable electronic device and operable to collect a set of information related to the user;

wherein the mobile communication device or the wearable electronic device is operable to measure circadian rhythm and duration of sleep of the user; and a processing module configured to communicate with at least one of the mobile communication device and the wearable electronic device, the processing module operable to:

receive the set of measurement data related to the user from the wearable electronic device;

receive the set of information related to the user from the mobile communication device;

receive the measured circadian rhythm and duration of sleep of the user from the wearable electronic device or the mobile communication device;

determine sleep scores for a predefined number of days, wherein a sleep score is determined for each of the predefined number of days from the collected set of information, the set of measurement data, the circadian rhythm and the duration of sleep of the user, and associate each sleep score with a corresponding go-to-bed time or time of falling asleep of the user;

analyse the sleep scores and associated go-to-bed time or time of falling asleep of the user to determine an optimum bedtime window for the user; and provide feedback to the user on the mobile communication device, based on the analysed sleep scores and the optimum bedtime window, wherein the feedback comprises instructions to the user related to adjusting the sleep pattern.

The present disclosure provides the aforementioned method for providing feedback to a user for adjusting sleep pattern of the user. The described method provides a gradual adjustment of sleep pattern of the user in order to achieve the optimal go-to-bed time and wake-up time, thus without causing any stress around the sleeping hours. The described method is adaptive and considers the user's health and daily activities in providing the optimal go-to-bed time and wake-up time. Consequently, the described method provides a personalized approach in providing a healthy sleep pattern to the user. Furthermore, the system described herein is seamless, simple and easy to implement. In the present disclosure, the term "sleep score" relates to a score provided to a sleep that the user may obtain in a span of a day (namely, a duration of 24 hours). Moreover, contrary to what is disclosed in document U.S. 2017/132946, the present method and system defines an optimal go-to-bed time related to a high sleep score, and does not merely draw conclusions on past actions. Indeed, a person's sleep score varies strongly from a person to person. Thus, it is valuable to define such a dependence between sleep score vs. go-to-bed time for each user personally. The system then provides feedback and instruction for the user for reaching optimal sleep score by guiding him/her to use optimal go-to-bed time to reach the desired high sleep score.

The method for providing feedback to the user comprises receiving a set of measurement data related to the user from the wearable electronic device. Notably, the wearable electronic device comprises means for measuring a set of measurement data related to the user. Specifically, the set of measurement data may comprise heart rate, movement of the user, body or body skin temperature, breathing rate and so forth. The wearable electronic device may comprise at least one sensor as a means for measuring the set of measurement data related to the user. Furthermore, the at least one sensor may be selected from a group consisting of an accelerometer, a gyroscope and a magnetic field sensor, for measuring user's movements. Additionally, the heart rate may be measured using a photon (for example infrared) source and a photon detector also arranged on an inner surface of the wearable electronic device. Additionally, the wearable electronic device may comprise a light sensor arranged on an outer surface of the wearable electronic device for measuring ambient light and a temperature sensor for measuring the body skin temperature of the user. The measured sensors data, such as the data of the motion sensor, the optical electronics, the light sensor and the temperature sensor, associated with the user and measured by the wearable electronic device may be further analysed to obtain the set of measurement data.

Concerning the circadian rhythm and the duration of sleep of the user, these can be either measured separately or calculated from the set of measurement data. I.e. the term "defining" in this context means both measuring and calculating. Various ways of obtaining this information are explained below.

In an embodiment, the set of measurement data related to the user can be received alternatively or additionally from a sensor arranged on a mobile device of the user, and/or from a sensor arranged in a premises, such as the bedroom. Likewise, the circadian rhythm and duration of sleep of the user can be measured by a sensor arranged on a mobile device of the user and/or by a sensor arranged in a premises. For example, a sensor for measuring the duration of sleep can be arranged in the bed of the user.

Optionally, the wearable electronic device is a ring configured to be suitably worn at a finger, such as an index finger, of the user. However, it may be evident to those skilled in the art that the system may be associated with other wearable electronic devices, such as a device adapted to be worn at wrist, chest and any suitable body part of the user, from where physiological data of the user can be measured. In such instance, the wearable electronic device may be configured to have a size to be suitably worn at such body parts of the user.

The method for providing feedback to the user comprises defining circadian rhythm and duration of sleep of the user. Specifically, the mobile communication device or the wearable electronic device is operable to measure circadian rhythm and duration of sleep of the user. The circadian rhythm is briefly the sleep/wake cycle. Specifically, the circadian rhythm may refer to physical, mental, and behavioural changes in the user that follow a daily cycle. More specifically, the user may experience a peak in energy levels at specific durations of time in a day. Similarly, the user may also experience a drop in energy levels at specific durations of time in day. Such changes in the user may influence an overall sleep pattern thereof. Furthermore, the rhythm and its changes in the user may be measured to estimate the circadian rhythm of the user.

Optionally, the duration of sleep is measured as a time between moment of falling to sleep and moment of waking up or as a time between moment of going to bed and moment of waking up, wherein said moments are determined based on at least one of pre-defined changes in heart rate, pre-defined changes in body or skin temperature and changes in movement of the user. For example, the duration of sleep of the user may be derived from a hypnogram. Alternatively, the duration of sleep of the user may be measured with the data from the motion sensor (i.e. when the user went to bed and woke up), which should be static or include minute variations (due to no physical provocations). Therefore, based on the data from the motion sensor, the duration of sleep of the user may be determined. Furthermore, the data from the motion sensor and the hypnogram may be correlated to measure the duration of sleep.

In an embodiment, the circadian rhythm may be measured using various sensor data. Furthermore, the circadian rhythm of the user may be affected by a chronotype of the user. As mentioned above, the wearable electronic device includes the light sensor capable of measuring illumination level as well as colour space. The colour space refers to visible frequencies of the light. For example, if the light sensor detects blue light then the light sensor considers the light to be day light. This can be used to determine if the ambient light is from artificial light or natural light. Further, the light sensor can be used to detect illumination conditions during the sleeping time and corrected therewith. Therefore, based on the data from the light sensor, the temperature sensor and the sleeping pattern measurements, a circadian rhythm of the user can be measured. The circadian rhythm may include information such as at around 2 AM the user gets deepest sleep, at 4:30 AM the user has lowest core body temperature (low resting heart rate may be used as an indication of low core body temperature), at around 6:45 AM the user has sharpest blood pressure, and so forth.

According to an embodiment, the wearable electronic device measures the skin temperature of the body, wherein skin temperature of the user may differ from the core body temperature, and wherein skin temperature typically varies in comparison with the core body temperature. For example, a rise in the skin temperature in the evening is associated with a drop in the core body temperature. Moreover, an increase in the skin temperature may be a marker of circadian rhythm of the user.

According to an embodiment, the wearable electronic device also includes electronic components configured to collect and analyse data from the at least one sensor. For example, the wearable electronic device may include other electronic components which may include but not limited to a controller, a microprocessor, a memory and a communication module. The controller is operable to control operation of the at least one sensor for generating data related to the user's movement, heart rate, body and/or skin temperature and ambient light (the user is subjected to). The microprocessor may be operable to process or analyse collected data generated by the at least one sensor. Furthermore, the memory is used for storing the analysed or processed data. Moreover, the communication module is configured to establish a communication between the wearable electronic device and the mobile communication device. For example, the mobile communication device may be wirelessly connected to the wearable electronic device by a wireless connection such as a Wi-Fi, Bluetooth and so forth. Furthermore, the mobile communication device is intended to be broadly interpreted to include any electronic device that may be used for voice and/or data communication over a wireless communication network. Examples of mobile communication devices include, but are not limited to, cellular phones, personal digital assistants (PDAs), handheld devices, wireless modems, laptop computers, personal computers and so forth. Additionally, the mobile communication device includes a casing, a memory, a processor, a network interface card, a microphone, a speaker, a keypad, and a display.

The method for providing feedback to the user comprises collecting a set of information related to the user. Specifically, the mobile communication device is operable to collect the set of information related to the user. Specifically, the set of information may comprise information such as height, weight, age, gender, location and so forth related to the user. Specifically, the user may manually input information related thereto in the mobile communication device.

Optionally, the set of information comprises physiological performance related information based on an external data input by the user. Furthermore, the physiological performance related information may be derived from the physiological data (or parameters) of the user measured by the wearable electronic device, such as heart-rate-variability, a respiration rate, a sleeping pattern of the user, a hypnogram, user's stress level and so forth. Additionally, optionally, the physiological performance related information is biased or influenced by some external data (or factor), which are different from internal data, such as the biological signals or physiological data associated with the user.

In an embodiment, the external data comprises at least one of travel information, time zone, calendar, working schedule, and holidays. The external data may be received from the user as user input with the help of the mobile communication device. For example, the mobile communication device may be provided with various user interfaces associated with such external data allowing the user to make selection for the external data. Furthermore, the mobile communication device may include sensors, such as location sensor (GPS) to determine the location of the user, i.e. if the user has travelled some distance and moved out of his city/country. Further, the travel may be such of a nature that may influence sleep of the user. For example, a travel plan which requires travelling in night, travelling to different time zones, or travelling in difficult conditions, such as rough terrain. Moreover, the travel plan may include bus journeys or journey by water vessel, i.e. for instances when the user travel by bus or ship for a substantial distance, and their times. Additionally, the information of the travels may be such that they may influence the physiological state (parameters or data) of the user when associated with the current travel. In an example, the information of the travels may be comparatively recent (for example few days, a week or a month), such that when the user takes the current travel (or a new travel) the information of the past travels and the future travels may influence the sleep of the user.

In an embodiment, the mobile communication device and the processing module are configured to collect data from at least one sensor generated by the wearable electronic device. Furthermore, the mobile communication device and the processing module are configured to perform analysis of the data from at least one sensor in order to find heart rate variability, hypnogram, stress level, sleep duration, circadian rhythm and the like. For example, the analysis may be performed partly by the mobile communication device and partly by the processing module. Alternatively, entire analysis may be performed by the mobile communication device.

Throughout the present disclosure, the term "processing module" relates to a structure and/or module that include programmable and/or non-programmable components configured to store, process and/or share information. Optionally, the processing module includes any arrangement of physical or virtual computational entities capable of enhancing information to perform various computational tasks. Furthermore, it will be appreciated that the processing module may be both single hardware module and/or plurality of hardware modules operating in a parallel or distributed architecture. In an example, the processing module may include components such as memory, a processor, a network adapter and the like, to store, process and/or share information with other computing components, such as the mobile communication device. Optionally, the module is implemented as a computer program that provides various services (such as a database service).

The processing module is further configured to communicate with at least one of the mobile communication device and the wearable electronic device. For example, the processing module is communicatively coupled to the mobile communication device and/or the wearable electronic device through a network which can be wired, wireless or a combination thereof. For example, the network includes, but is not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, and Worldwide Interoperability for Microwave Access (WiMAX) networks.

The method for providing feedback to the user comprises determining sleep scores for a predefined number of days, wherein a sleep score is determined for each of the predefined number of days from the collected set of information, the set of measurement data, the circadian rhythm and the duration of sleep of the user and associating each sleep score with a corresponding go-to-bed time or time of falling asleep of the user. The term associating in this context means comparing the relationship on the go-to-sleep time or falling asleep time to the sleep score for the night. Specifically, the processing module is operable to receive the set of information related to the user from the mobile communication device, receive the set of measurement data related to the user from the wearable electronic device, and the measured circadian rhythm and duration of sleep of the user from the wearable electronic device or mobile communication device. The processing module is operable to determine sleep scores for a predefined number of days. More specifically, the processing module may be operable to analyse the received parameters for the user to determine a sleep score of a sleep of the user. Furthermore, each of the sleep score of the user for each of the predefined days is associated with the go-to-bed time or time of falling asleep of the user.

In an embodiment, the processing module is further operable to store the measured circadian rhythm and the measured duration of sleep. For example, the measured circadian rhythm and the measured duration of sleep may be stored in a database of the processing module. In an embodiment, the operation and working of the processing module and the database can be implemented with a dedicated computer system, a cluster of computers and a cloud service. Furthermore, the stored information combined to an input by the user is used in a step of re-calibration of the wearable electronic device. As mentioned above, the input by the user may be associated with the external data, which comprises at least one of travel information, time zone, calendar, working schedule, and holidays.

In an embodiment, the mobile communication device or the wearable electronic device comprises the processing module. In such example, the wearable electronic device and/or the mobile communication device may include components such as a memory, a storage unit, a display, a processor, a network and so forth. Typically, the wearable electronic device and/or the mobile communication device is operable to analyse the received data such as the set of information, the measurement data, the measured circadian rhythm and the duration of sleep. Furthermore, the wearable electronic device and/or the mobile communication device is operable to generate an optimum bedtime window and consecutive feedbacks for the user. The feedback provided to the user may include a message in form of a pop-up notification, message notification and so forth. Furthermore, the feedback provided to the user may include a message relating to the optimum bedtime of the user. In practice, the feedback may be provided to the user for example in the form of a message shown in the wearable electronic device and/or the mobile communication device, or it may be in the form of a text message to the mobile communication device. It may also be a combination of for example a sound or vibration alert of the wearable device or the mobile communication device, alerting the user to consult the feedback. The system may further comprise for example such an alert at a pre-defined moment before the determined optimal bedtime, such as one hour or half an hour before. This pre-defined moment may also be such that the user can set it her/himself.

Optionally, the processing module may be implemented using a server arrangement, wherein the server arrangement is communicably coupled to the mobile communication device and/or the wearable electronic device. Furthermore, the server arrangement may be implemented in a cloud environment.

It will be appreciated that the term "bedtime" as used herein relates to a go-to-bed time of the user. Specifically, the go-to-bed time relates to a time of going to bed for the user. Furthermore, the bedtime of a user is different from a time of falling asleep of the user. However, in the scope of this invention, both the go-to-bed time and time of falling asleep can be used for analysing the optimum bed time and guiding a user to find an optimal bedtime to reach an optimal sleep score. The term "bedtime" is used interchangeably with the term "go-to-bed time" and "moment of going to bed", wherever appropriate i.e. whenever one such term is used it also encompasses the other term.

In the present disclosure, the term "sleep score" may relate to a score provided to a sleep that the user may obtain in a span of a day (namely, a duration of 24 hours). Specifically, the sleep score of the sleep of the user may be based at least one of: a time of falling asleep, a bedtime of the user (namely, a go-to-bed time), wake-up time, circadian rhythm and physical parameters of the user, quality of the sleep, sleep onset latency and so forth. In an example, the sleep score may be numerical score and/or an alphabetic or an alphanumeric grade. Specifically, the numerical score may be determined on a scale of zero to 100. In such example, a numerical score higher than 80 may be indicative of an optimum sleep duration and quality. Similarly, in such example, a numerical score lower than 70 may be indicative of a low sleep duration or low sleep quality or both. Furthermore, the user may obtain a high sleep score by sleeping an adequate amount of hours during a time window that is good for sleep, according to the user's circadian rhythm.

By "quality of the sleep" in this description it is meant the quality of the nightly sleep period. The quality of the sleep is considered to be high when the (relative or absolute) amount of deep sleep is sufficient and/or when the (relative or absolute) amount of REM-sleep is sufficient, and/or when the user has slept uninterrupted for 90-100 minutes for 4-6 times during the night, and/or the user has had limited amount of movement during the sleep, and/or the number of waking ups during the night (either as an absolute number or per unit of time) is low enough. Some of these characteristics are considered relatively universal, for example the requirement of "sufficient amount of REM-sleep" for the sleep to be considered of a good quality is approximatively the same for every person. Other characteristics may slightly vary from one user to another, but the variations are typically quite small.

Optionally, the duration of sleep is a determinant of the sleep score. Furthermore, the duration of sleep is the length of time between the moment of falling asleep and the wake-up time. In such example, the sleep score may be 100 for a sleep duration of nine hours or more. Similarly, in such example, the sleep score may be 0 for a sleep duration of three hours or less.

More optionally, the sleep score can be altered depending on the set of information provided by the user. In one example, the age of the user can be used to alter the sleep score. In such example, for a user b with an age of 80 years, the sleep score may be 100 for a sleep duration of 8 hours.

In an embodiment, the processing module is operable to determine the sleep efficiency of the user. Specifically, sleep efficiency is indicative of a quality of sleep of the user. More specifically, the sleep efficiency may be based on factors such as movement of the user while asleep (indicative of restlessness and wake-ups while in bed), duration of sleep in a deep sleep stage, rapid eye movement data, hypnogram and so forth. Furthermore, the sleep efficiency may be a numerical grade. Optionally, the processing module is operable to determine the sleep efficiency based on the set of measurement data received from the wearable electronic device.

The bedtime of a user and the moment of falling asleep of the user may be determined using measurement data. Measurement data such as movement data, body skin temperature data, heart-beat rate data and skin conductivity may be analysed over a predetermined period. Additionally, the predetermined period may range from 1 minutes to 4 minutes. Furthermore, if one of the parameters such as the movement of the user drops for a predetermined period of time, then other parameter such as heart rate is analysed to determine if the user is in bed or asleep In an example, the bedtime of a user is 10:00 PM. In such example, a combination of high body skin temperature data (such as higher than 34 QC) over a predetermined amount of time and low movement of the user data (such as less than 3 to 7 movements) over a predetermined amount of time indicates higher probability of subject being in bed. Additionally, long heart-beat intervals (such as low heart rate between 40 to 60 bpm) also indicate high probability of the user being in bed. In another example, the wake-up of a user is 8:00 AM. In such example, a combination of high movement of the user (such as higher than 25 movements) over a predetermined amount of time, low body skin temperature (such as lower than 34 QC) and shorter heart-beat intervals (such as below 950 ms, corresponding with heart rate higher than 63 bpm) over a predetermined amount of time indicates the user being out of bed. Additionally, the activity of user being in bed or out of bed can be detected using electrodermal activity (EDA) data.

The method for providing feedback to a user for adjusting sleep pattern of the user comprises analysing the sleep scores and associated go-to-bed time and/or time of falling asleep of the user to determine an optimum bedtime window for the user. The processing module is operable to analyse the sleep score and associated go-to-bed time and/or time of falling asleep of the user to determine an optimum bedtime window for the user. Specifically, the processing module is operable to determine a length of the optimum bedtime window and start time and end time of the optimum bedtime window. More specifically, the sleep scores of the predefined number of days are analysed to determine the optimum bedtime window. Moreover, the optimum bedtime window may have the highest number of high sleep scores in the predefined number of days.

Throughout the present disclosure, the term "optimum bedtime window" relates to a window (namely, timepoint and duration) of time in which it may be ideal for a user to fall asleep. Specifically, a sleep of a user may have a high probability of obtaining a high sleep score (and, sleep efficiency) if the user falls asleep in the optimum bedtime window. Furthermore, the optimum bedtime window may be determined at least based on the circadian rhythm, physical parameters, physical and mental activity and so forth of the user. Optionally, the length of the optimum bedtime window ranges from 0 minutes to 60 minutes. In some implementations, the length of the optimum bedtime window may be, for example, 0, 10, 20, 30, 40, 50, 60, 70, 80, or 90 minutes.

The optimum bedtime window can be considered as an optimum bedtime and time variation (i.e. time window) around the optimum bedtime. The defined time variation can be set before or after or middle of the optimum bedtime. The optimum bedtime window can be also without setting any time range as such. Then the optimum bedtime window is just optimal bedtime (timepoint) Specifically, the optimum bedtime window is determined based on variation of bedtimes of the user in the predefined number of days. According to an embodiment, it is possible to primarily indicate a moment of time (a timepoint) which is the optimum time to go to bed, i.e. to fall asleep quickly. It is also possible to set, secondarily, a time frame (a time window) in which it is advantageous for the user to go to bed.

The method for providing feedback to the user comprises analysing the sleep scores to determine an optimum bedtime window for the user. Specifically, the optimum bedtime window may only be determined after analysing the sleep scores for the predefined number of days. More specifically, the optimum bedtime window during the predefined number of days may be designated as a default go-to-bed time. In an example, the optimum go-to-bed time during the redefined number of days may be designated a default to be 10:30 PM. Furthermore, the optimum go-to-bed time may be determined after the predefined number of days based on the variability in the daily go-to-bed time of the user. Additionally, the processing module is operable to determine an optimum bedtime in the optimum bedtime window, wherein the user may be obtaining the highest sleep scores in the predefined days by sleeping at the optimum bedtime. In an example, the optimum bedtime window for a user "X" may be 10:30 PM to 11:30 PM. In such example, the optimum bedtime for the user "X" may be 11:00 PM.

In an embodiment, the processing module is operable to determine the length of the optimum bedtime window by analysing the sleep scores. Specifically, the length of the optimum bedtime window may only be determined after analysing the sleep scores for the predefined number of days. More specifically, the length of the optimum bedtime window during the predefined number of days may be designated as a default duration. In an example, the length of the bedtime window during the predefined number of days may be designated a default duration of 60 minutes. Furthermore, the length of the optimum bedtime window may be determined after the predefined number of days based on the variability in the daily go-to-bed time of the user. Specifically, the variability in the daily go-to-bed time of the user may be defined as the time difference between the earliest go-to-bed time and the latest go-to-bed time. In an example, the variability in the daily go-to-bed time for a user with the earliest go-to-bed time at 10:30 PM and latest go-to-bed time at 11:15 PM is 45 minutes. In an implementation, if the variability of the user is less than 45 minutes, the length of the optimum bedtime window may be determined as 30 minutes. In such implementation, if the variability of the user is higher than 45 minutes and lower than 67 minutes and 30 seconds, the length of the optimum bedtime window may be determined as 45 minutes. Furthermore, in such implementation, if the variability of the user is higher than 67 minutes and 30 seconds, the length of the optimum bedtime window may be determined as 60 minutes.

In an embodiment, the processing module is operable to define the predefined number of days. Specifically, the predefined number of days may be defined based on a number of sleep scores required to determine the optimum bedtime window for the user. Furthermore, the processing module is operable to discard sleep scores of days that may not be routine for the user. Therefore, such days may not be considered in the predefined number of days. Specifically, the processing module may discard sleep scores for days in which the user may travel across time-zones as sleep schedule of the user may be disrupted due to jetlag. Moreover, the processing module may discard sleep scores for days when the user has an abnormal heart rate. Furthermore, the processing module may be operable to determine a routine wake-up time of the user. Consequently, the processing module may only analyse sleep scores for days when the wake-up time of the user is within 30 minutes of usual wake-up time thereof. Additionally, the user may be operable to adjust the routine wake-up time thereof, wherein the adjusted wake-up time may be within a range of the determined routine wake-up time. In an example, such range is 30 minutes. Optionally, the processing module may be operable to define a minimum predefined number of days. Specifically, the processing module is operable to analyse sleep scores of at least the minimum predefined number of days to determine the optimum bedtime window. Furthermore, the processing module may also analyse sleep scores of days after the minimum predefined number of days. However, the processing module is operable to consider sleep scores of the most recent predefined number of days. In an example, the predefined number of days is 30 days. In such example, the minimum predefined number of days is 7 days. Therefore, in such example, the minimum number of sleep scores required to be analysed to determine the optimum bedtime window is 7. Furthermore, in such example, the processing module may analyse data of the most recent 30 days to determine the optimum bedtime window, wherein the number of sleep scores require to determine the optimum bedtime window is 7. Furthermore, optionally, the optimum bedtime window is adaptable to changing go-to-bed times and wake-up times of the user. Specifically, the optimum bedtime window may be updated when the sleep schedule (i.e., go-to-bed times and wake-up times) are subject to change.

The method for providing feedback to a user for adjusting sleep pattern of the user comprises providing feedback to the user based on the analysed sleep scores and the optimum bedtime window, wherein the feedback comprises instructions to the user related to adjusting the sleep pattern. The processing module is operable to provide feedback to the user on the mobile communication device based on the analysed sleep scores and the optimum time window. Specifically, the instructions to the user may relate to improving bedtimes (specifically, go-to-bed time, wake-up time), sleep efficiency, sleep scores and so forth of the user. Furthermore, the feedback may comprise information on ways the user may improve sleep pattern thereof. In an embodiment, the feedback may be a text or a voice message provided on the mobile communication device regarding the sleep pattern of the user. In an example, the feedback may comprise instructing user to perform light exercise in the day prior to the sleep to obtain a higher sleep score. Optionally, the processing module is operable to provide a feedback on the wearable electronic device.

In an implementation, the sleep scores for the predefined number of days are received. Therefore, the length of an optimum bedtime window is determined based on the variability in the daily go-to-bed time of the user. Consequently, bedtime windows are analysed with increments of 15 minutes based on the determined length of the optimum bedtime window. In an example, the earliest go-to-bed time of the user is 10:30 PM and the latest go-to-bed time is 12:30 PM. Therefore, in such example, the determined length of the optimum bedtime window is 60 minutes. Furthermore, in such example, sleep scores of bedtime windows such as 10:30 PM to 11:30 PM, 10:45 PM to 11:45 PM, 11:00 PM to 12:00 PM, 11:15 PM to 12:15 PM and 11:30 PM to 12:30 PM are analysed. Therefore, in the implementation, after such analysis, a bedtime window with highest values of sleep scores is identified. Furthermore, the number of sleep scores with highest values should be higher than a threshold number. Consequently, a bedtime window with highest values of sleep scores is identified. In such implementation, the sleep score is determined based on a numerical score on a scale of zero to 100. In such implementation, sleep scores of the bedtime window with higher values of sleep scores are analysed. Consequently, a highest value of sleep score is identified from higher values of sleep scores. In an example, a bedtime window of 10:45 PM to 11:45 PM is identified comprising higher values 77, 79, 80, 83, 85 of sleep scores. Therefore, in such example, the highest value 85 from the higher values of sleep scores is identified. Optionally, the bedtime window with the higher values of sleep score is determined to be the optimal bedtime window.

In a specific case of the implementation, when the highest value of sleep score identified is greater than or equal to 85, the preceding and/or succeeding bedtime windows are analysed. Consequently, when the preceding and succeeding bedtime windows exhibit sleep scores is in consistence with higher values of the sleep scores in the identified bedtime window, the length of the bedtime window may be extended to include the preceding and/or succeeding bedtime windows. However, the length of the bedtime window may not be extended greater than 30 minutes. Therefore, the bedtime window obtained after analysis of succeeding and preceding bedtime windows is determined to be the optimum bedtime window.

In another specific case of the implementation, when the bedtime window with the higher values of sleep scores is the first bedtime window (i.e. 10:30 PM to 11:30 PM), the highest value of sleep score is identified. Consequently, in an example, if the highest value is greater than 75, it may be inferred that the user obtains high sleep score at early go-to-bed times. Therefore, a feedback may be provided to the user recommending earlier go-to-bed times or later wake up times. Alternatively, in another example, if the highest score identified is lesser than 75, the sleep efficiency of the user may be analysed. In such example, if the sleep efficiency is higher than a threshold, a feedback may be provided to the user recommending to spend more time in bed (i.e. earlier go-to-bed times and/or later wake-up times). Furthermore, in such example, if the sleep efficiency of the user is lower than the threshold, a feedback recommending an appropriate sleep program may be provided.

In yet another specific case of the implementation, when the highest value of sleep score is lesser than 85 and greater than 75, a feedback recommending a later wake-up time may be provided to the user.

Throughout the present disclosure, the term "sleep pattern" relates to routine pattern in sleep of the user. Furthermore, sleep pattern also relates to a biological rhythm that guides body regarding go-to-bed time and wake-up time thereof. Additionally, sleep pattern typically follows a 24-hour cycle, controlling the user's schedule for go-to-bed time and wake-up time. Moreover, a healthy sleep pattern is associated with an optimum sleep and wake-up schedule. Specifically, such sleep pattern generates higher sleep score and provides higher sleep efficiency.

Optionally, the method further comprises storing a set of parameters related to sleep patterns. Optionally, the processing module is operable to store the set of parameters related to sleep patterns. Specifically, such parameters may include information on activities, dietary conditions, room temperatures, physical conditions and so forth that may help in inducing sleep. Furthermore, such parameters may include durations of sleep required for a user based on physical parameters (such as weight, height, age and so forth) and physical activity thereof. Additionally, the processing module may store information related to circadian rhythms, monophasic, biphasic and poly-phasic sleep cycles.

Optionally, providing the feedback is further based on a set of measurement data for a consecutive day. Optionally, the wearable electronic device is operable to measure a set of measurement data for a consecutive day. The consecutive day is succeeded by the predefined number of days. Specifically, the consecutive day is succeeded by the minimum predefined number of days required to determine the optimum bedtime window of the user. Therefore, after determining the optimum bedtime window for the user, the wearable electronic device is operable to measure the set of measurement data for the consecutive day. Specifically, the set of measurement data for the consecutive day may include, but is not limited to, sleep scores of the sleep of consecutive day and physical activity of user in the consecutive day, go-to-bed and wake-up times of the user, and external factors such as calendar, working schedule, holidays, time zone for the consecutive day and travel information. Consequently, the set of measurement data for the consecutive day may provide information related to the daily activities of the user.

Optionally, the processing module is operable to provide the feedback further based on the set of measurement data for the consecutive day. Specifically, the processing module is operable to analyse the set of measurement data for the consecutive day and determine the information related to the daily activities of the user. Subsequently, the processing module is operable to provide feedback based on the daily activities of the user. In an example, the processing module may determine a hectic work schedule of the user. Therefore, in such example, the processing module may provide on the mobile communication device (or the wearable electronic device), a feedback recommending "Go to bed early". Consequently, in such example, the user may be able to recover from the hectic work schedule. In another example, the processing module may determine, from the set of measurement data of the consecutive day, a day with low physical activity of the user. Therefore, in such example, a feedback recommending "Go for a walk" may be provided to the user. In yet another example, the processing module may determine an improper sleep schedule of the user for a plurality of consecutive days. Consequently, in such example, the processing module may provide a feedback recommending longer duration of bedtime to improve the sleep schedule. Furthermore, the processing module may be operable to change the optimum bedtime window and the wake-up time of the user based on set of measurement data for the consecutive day.

Optionally, the processing module is operable to analyse go-to-bed times for a plurality of consecutive days and determine a median go-to-bed time. Subsequently, the processing module is operable to compare the median go-to-bed time of the user and the optimum bedtime window. In an example, when the median bedtime for 15 days is in the optimum bedtime window, a feedback "Good work. Keep it going!" may be provided to the user on the mobile communication device. In another example, when the median bedtime of the user is in a range of 30 minutes as compared to the optimum bedtime window, a feedback "Go to bed early" or "Go to bed late" may be provided to the user. In yet another example, when the median bedtime of the user is not in the optimum bedtime window or in a range of 30 minutes, a feedback recommending an appropriate sleep program may be provided to the user.

Optionally, the user is operable to provide an input using the mobile communication device and/or the wearable electronic device. Specifically, the input by the user is based on at least one of answer to at least one question. In an example, the at least one question may include "How are you feeling", "How was your sleep" and "Are you feeling stressed", and their possible answers may be "Feeling fresh", "Good" and "No", respectively. The answer to at least one question may be subjective in nature and primarily based on how the user is feeling about his/her physiological state. Furthermore, the processing module is operable to determine the sleep efficiency based on the input by the user. In an example, when the user input to the question "How are you feeling" after a sleep of duration of 6 hours is "Feeling fresh", the processing module may determine a high sleep efficiency and/or sleep score.

In an embodiment, the feedback provided to the user may be based on shifting of circadian rhythm due to travelling. In an example, the system detects a 7 hour advance in local time indicating that the user has travelled across the time zones eastwards (e.g. from Denver to London). Furthermore, the system takes into account the user's circadian rhythm indicating that the user has high energy levels in mornings. The system therefore gives the instructions to the user to stay in dark room and sleep between 11 PM and 7 AM (local time), avoid ambient light before noon, seek ambient or artificial light after noon, avoid exercise before noon, and eat according to the local meal times. Accordingly, the wearable electronic device measures shifting of the circadian rhythm (i.e. detects or measures circadian rhythm alignment) using following sleep parameters: bedtime, sleep onset time, sleep onset latency, awakening time, sleep midpoint, deep sleep midpoint, and REM sleep midpoint. Furthermore, the wearable electronic device modifies the instructions for the following days according to the measured amount of shifting. The wearable electronic device also measures ambient light exposure in order to modify the instructions according to the user's behaviour. If the user may not be able to avoid light exposure before noon, the system guides the user to delay the rhythm instead of advancing during the following days. Furthermore, the feedback may be provided on the wearable electronic device, wherein a graphical user interface of the wearable electronic device is operable to display the feedback.

Optionally, providing the feedback is further based on a set of measurement data for a consecutive day, wherein the consecutive day is succeeded by the predefined number of days. Optionally, the duration of sleep is measured as a time between moment of falling to sleep and moment of waking up, wherein said moments are determined based on at least one of pre-defined changes in heart rate, pre-defined changes in body skin temperature and changes in movement of the user. More optionally, the set of information comprises physiological performance related information based on an external data input by the user. Optionally, the external data comprises at least one of travel information, time zone, calendar, working schedule and holidays. Optionally, the method further comprises storing a set of parameters related to sleep patterns.

One example of a method for determining a sleep score, is as follows. Firstly, a total amount of sleep is determined and the total amount associated with a number of additional inputs is determined. The total amount of sleep consists at least of the duration of sleep. It can also comprise sleep quality measures such as sleep phases, order of the sleep phases, duration of the sleep phases etc. The additional inputs of the sleep of the user may be based for example on at least one of: a time of falling asleep, a bedtime of the user (namely, a go-to-bed time), a wake-up time, circadian rhythm and physical parameters of the user, quality of the sleep, sleep onset latency, alignment of the sleep time with the sun and so forth. The additional inputs can be also an input from the user's physiological or personal information such as gender, weight, height, age, daily activity, fitness status and preferences such as habits to sleep. It is obvious that some inputs can be given by the user via the user interface of the mobile device, and some are preferably measured and/or determined by the wearable device or the mobile device.

Thereafter, a sub-score is determined for the total amount of sleep and total amount associated with the number of additional inputs. The sub score is in a range of 0-100. Furthermore, the sub-score is determined using suitable predetermined mapping function for each of the additional inputs and the total amount of sleep. Finally, the sleep score is calculated using the sub-scores for each of the additional inputs and the total amount of sleep. Additionally, the sleep score is calculated by taking median of the sub-scores determined for a sleep taken by a user. Furthermore, different averaging and summing methods may be employed for calculating the sleep score, wherein weightage of a given sub-score in the sleep score is higher than weightage of another given sub-score.

One example of a graphical representation of measurement data associated with a user over a day is given in the drawings. In general, one way of using such graphical representation is to detect the sleep duration of the user using the measurement data collected from the wearable electronic device. In an example, the sleep duration is determined using at least one of the measurement data such as the heart-beat rate (for example as heart beat-to-beat intervals in milliseconds), the body skin temperature (calculated for example using an equation: ((measured temperature-30) *100 in Celsius degrees) and the movement (for example as motions per minute*10). Such data can be used to plot the graph. Typically, the heart-beat rate is plotted in RR interval. Also, the body skin temperature may be scaled by ((TEMP-30)*100) for the plot. Moreover, the movement of the user may be tracked using a motion sensor such as an accelerometer coupled to the wearable electronic device. In an example, the moment of falling asleep is determined when there is a drop in the movement of the user. Furthermore, it is ensured that the user is in bed when there is an increase in the body skin temperature of the user and when there is a greater interval between the consecutive heart-beat rate (lower heart rate). Similarly, when there is an increase in movement of the user, a decrease in the body skin temperature and shorter interval between the consecutive heart-beat rate, it is concluded that the user is out of bed. Additionally, there are observed small changes in the movement of the user during the sleep duration. However, such movement correspond to the minor movements during sleep such as changing sides, changing positions and so forth. Moreover, the movements, heart rate changes, heart rate variability changes and/or skin temperature changes may be also associated to sleep phases during the sleep period. The system may be configured to use collected information and data to determine difference phases of the sleep, such as awake, REM-sleep, light sleep and deep sleep, in an accurate and reliable manner. The phases and their duration can be used as a part of the total amount of sleep or as an additional input.

The optimum bedtime window for the use can be shown in the graphical representation of sleep scores, for example by visual markers. One example of how such optimum bedtime window is determined is to plot the sleep scores corresponding to different bedtimes and to analyse the plot to determine a range that comprises high sleep scores. The time duration comprising the high sleep scores is accounted as the optimum bedtime window. Additionally or alternatively an optimal bedtime may be shown, again for example by a visual marker. Typically, the optimum bedtime corresponds to the highest sleep score and typically it yields maximum sleep efficiency. Also, good sleep efficiency is observed if the bedtime of the user lies within the optimum bedtime window. Moreover, data analysis for determining the optimum bedtime may be made by using fitted line to the data points and defining the line/curves maximum sleep score value. The corresponding bedtime is the optimal bedtime for the user.

The system and method may also comprise the use of a guiding program for a user. Typically, the guiding program can guide a user to go to the bed according to the current habits and latest activities of the user. The factors such as time of exercise, time of meal intake and so forth can indeed affect the bedtime of the user. In an example, if the user performs heavy or strenuous exercise then the user is advised to go to bed early owing to the physical activity. In another example, if the user has a heavy evening meal or dinner then the user may be advised to perform light exercise or go to bed a little late. The system may also advice the user to wind down, as a winding down time helps the user in relaxing and slowing down daily activities. Additionally or alternatively, the winding time can be set to be for example 60 minutes before the optimal bedtime window starts.

DETAILED DESCRIPTION OF THE DRAWINGS

Referring to FIG. 1, there is shown a schematic illustration of a system 100 for providing feedback to a user 102 for adjusting sleep pattern of the user 102, in accordance with an embodiment of the present disclosure. The system 100 comprises a wearable electronic device 104 configured to be worn by the user 102 and a mobile communication device 106 configured to communicate with the wearable electronic device 104. The system 100 further comprises a processing module 108 configured to communicate with at least one of: the mobile communication device 106 and the wearable electronic device 104.

Figure 2:
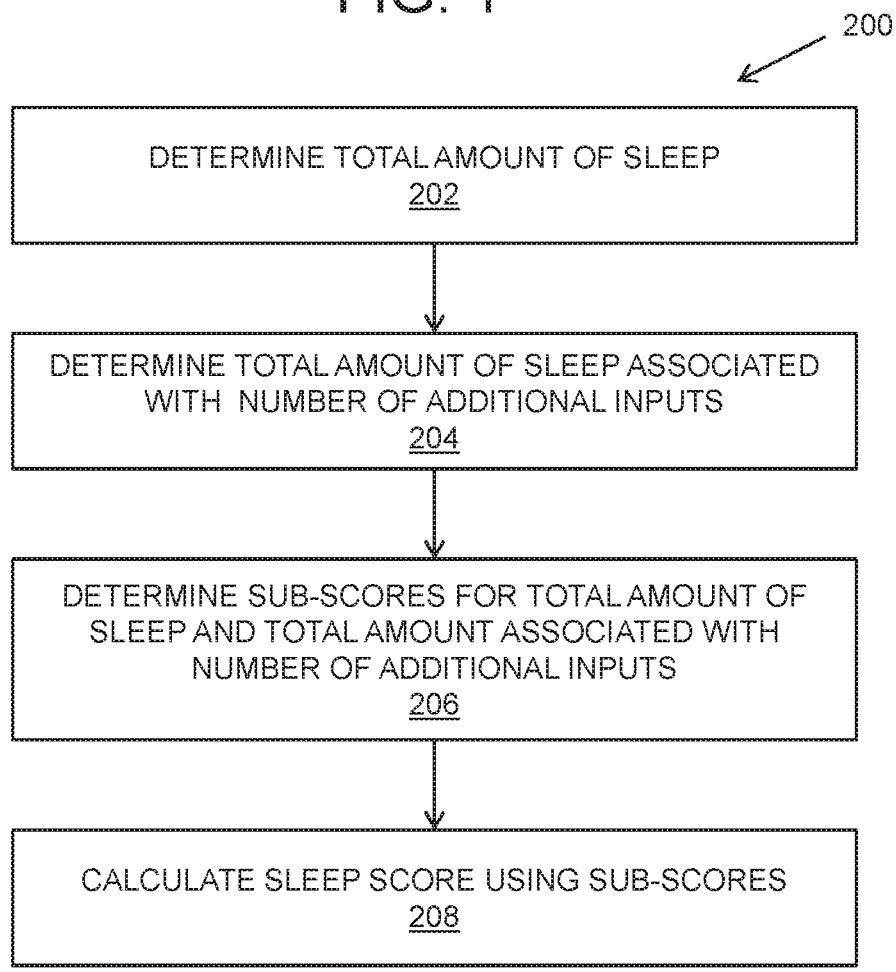
FIG. 2 is an illustration of steps of a method for determining a sleep score, in accordance with an embodiment of the present disclosure.

Referring to FIG. 2, illustrated are steps of a method 200 for determining a sleep score, in accordance with an embodiment of the present disclosure. At a step 202, a total amount of sleep is determined. At a step 204, a total amount associated with a number of additional inputs is determined. At a step 206, a sub-score is determined for the total amount of sleep and total amount associated with the number of additional inputs. At a step 208, the sleep score is calculated using the sub-scores for each of the additional inputs and the total amount of sleep. The steps 202 to 208 are only illustrative and other alternatives can also be provided where one or more steps are added, one or more steps are removed, or one or more steps are provided in a different sequence without departing from the scope of the claims herein.

Figure 3:
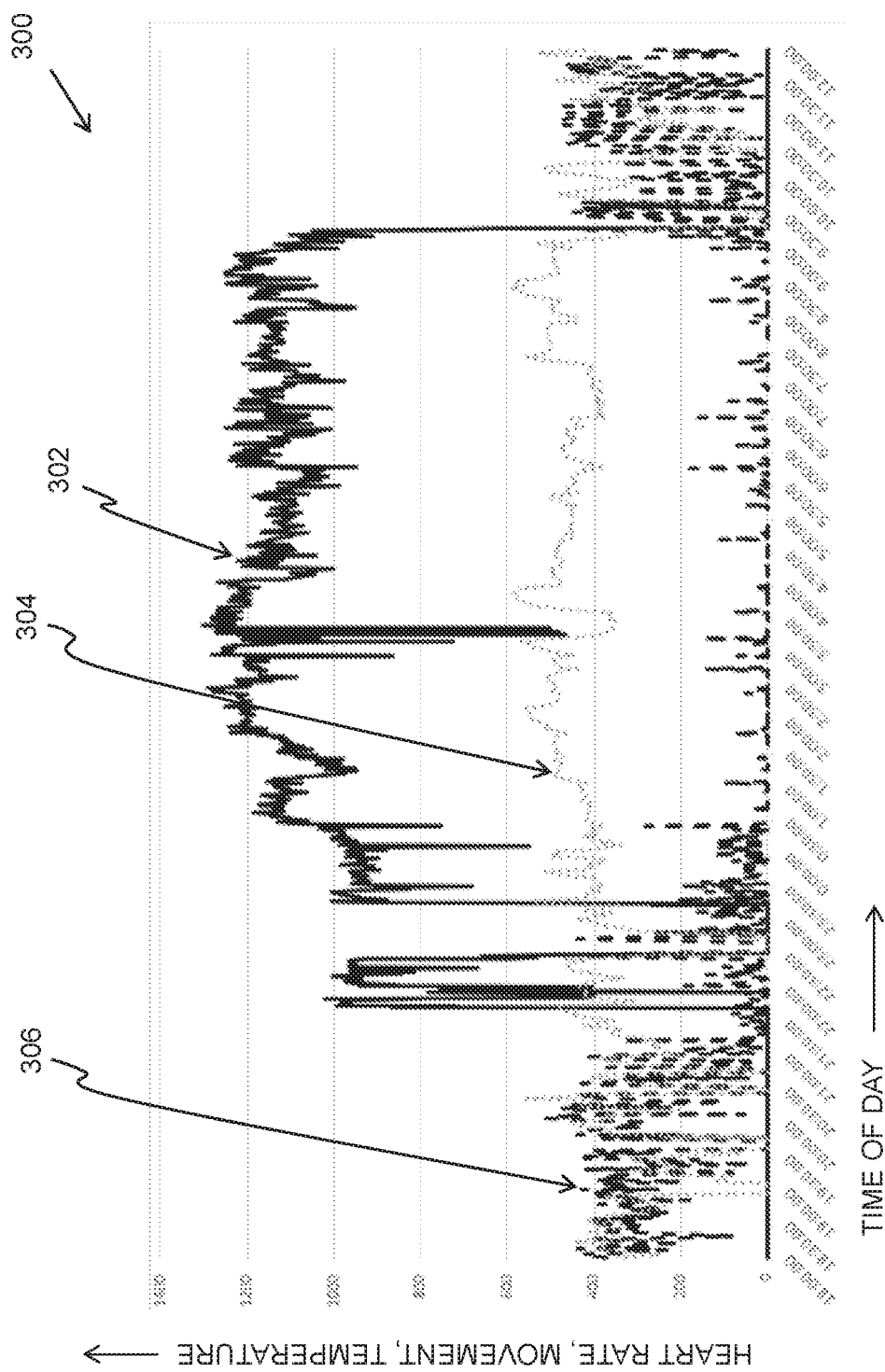
FIG. 3 is a graphical representation of measurement data associated with a user over a day, in accordance with an exemplary embodiment of the present disclosure.

Referring to FIG. 3, there is shown a graphical representation 300 of measurement data associated with a user over a day, in accordance with an exemplary embodiment of the present disclosure. In this example, the following information of the user are used to plot the graph: measurement data of the heart-beat rate 302 (shown as heart beat-to-beat intervals in milliseconds), the body skin temperature 304 (shown as calculated using ((measured temperature-30)*100 in Celsius degrees) and the movement 306 (shown as motions per minute*10). In this embodiment, the heart-beat rate 302 is plotted in RR interval, the body skin temperature 304 is scaled by ((TEMP-30)*100) for the plot and the movement 306 of the user is tracked using a motion sensor. As explained above, in this example, it is seen that the bedtime is 22:50 owing to decreased movement of the user, increased body skin temperature and slower hear rate. Furthermore, it seen that the wake-up time of the user is 8:30 owing to increased movement of the user, decreased body skin temperature and faster heart rate. Additionally, there are observed small changes in the movement of the user during the sleep duration.

Figure 4:
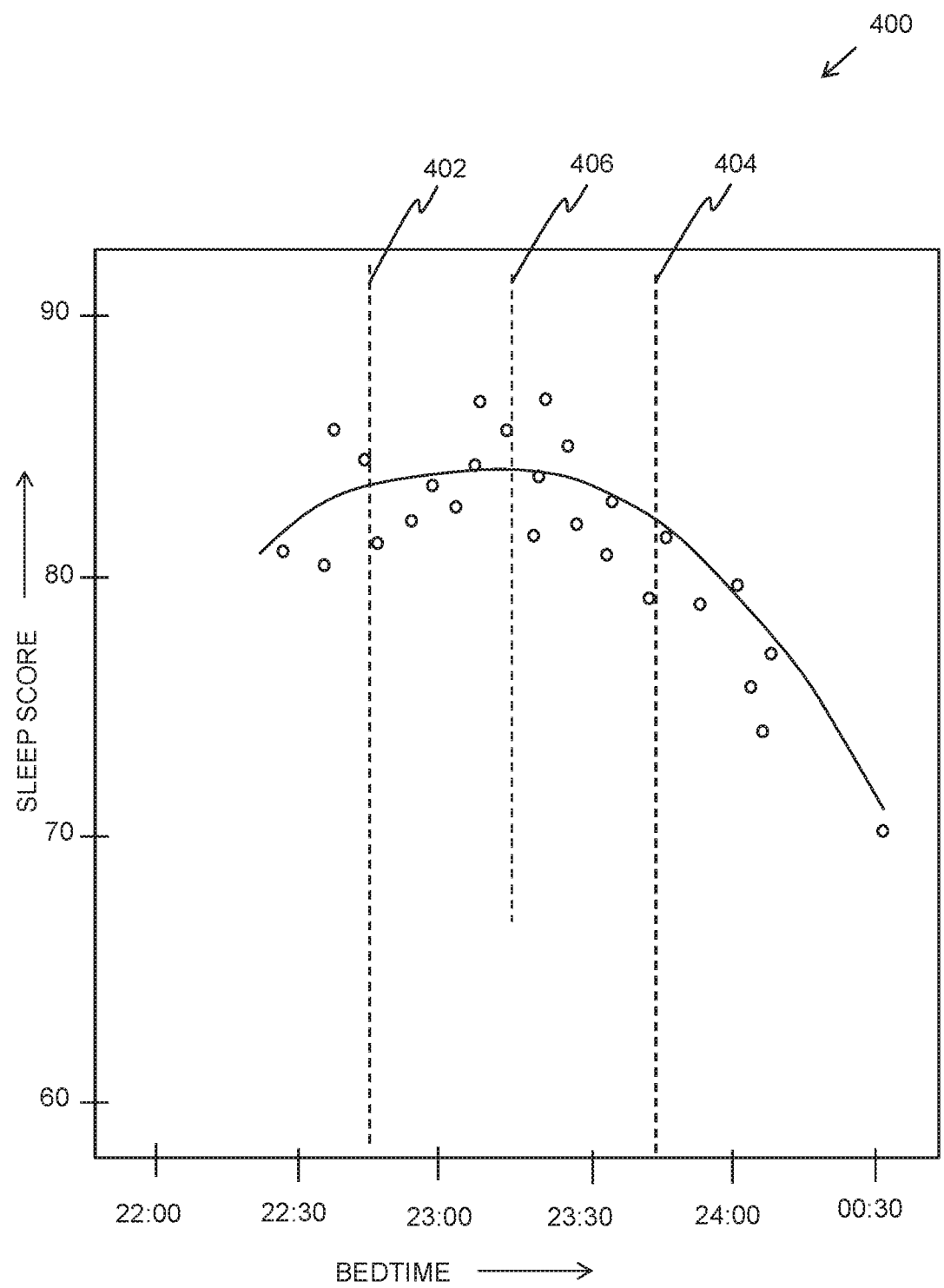
FIG. 4 is a graphical representation of sleep scores associated with bedtimes of a user, in accordance with an exemplary embodiment of the present disclosure.

Referring to FIG. 4, there is shown a graphical representation 400 of sleep scores associated with bedtimes of a user, in accordance with an exemplary embodiment of the present disclosure. Furthermore, the graphical representation 400 is used to determine the optimum bedtime window for the user, as shown using markers 402 and 404 in the graphical representation 400. Additionally, an optimal bedtime is shown by the marker 406. In this example, high sleep scores are detected between 22:50 and 23:50. In such case, 22:50 to 23:50 is considered as the optimum bedtime window. Furthermore, the highest sleep score in the optimum bedtime window corresponds to 23:15. Thus, 23:15 is defined as the optimum bedtime.

Figure 5A:
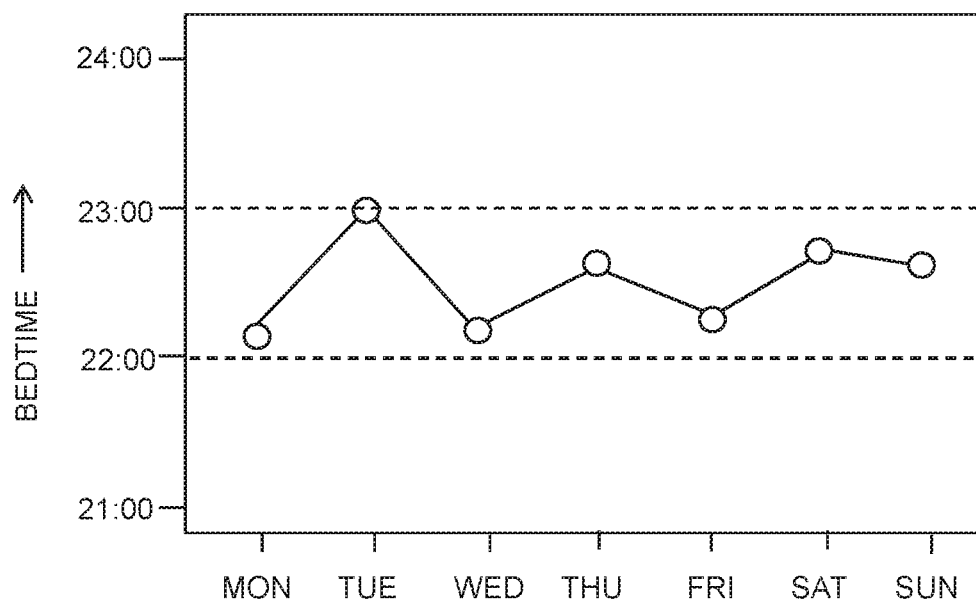
FIGS. 5A and 5B are illustrations of feedback associated with the bedtime of a user, in accordance with different exemplary embodiments of the present disclosure.
Figure 5B:
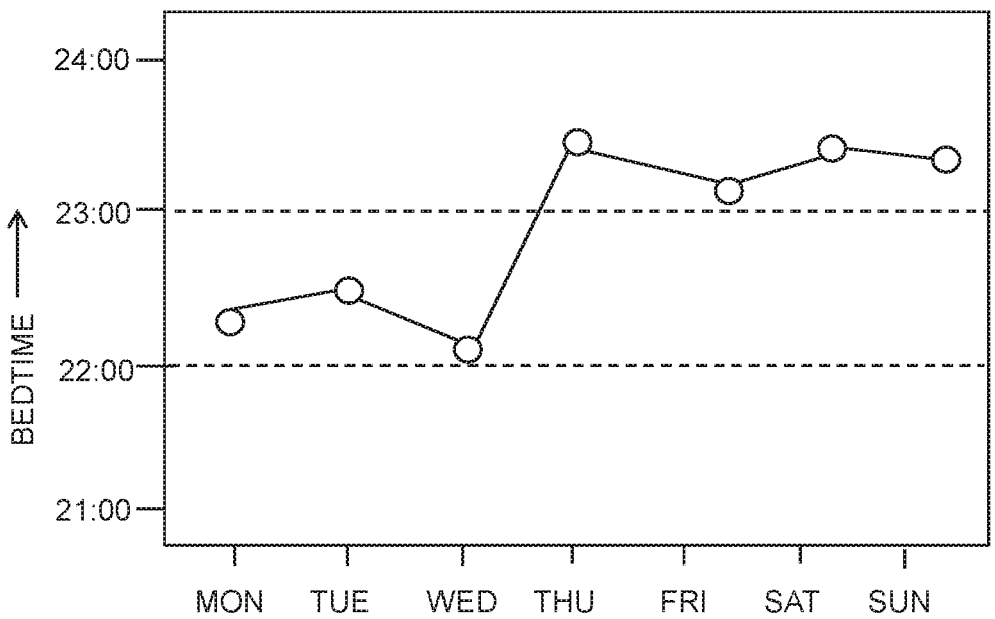

Referring to FIGS. 5A and 5B, there are shown illustrations of feedback associated with the bedtime of a user, in accordance with different exemplary embodiments of the present disclosure. Typically, the processing module acquires the daily bedtime of the user over a predefined number of days. Additionally, the acquired bedtime is analysed and a consecutive feedback is provided to the user. As shown in FIG. 5A, the bedtimes of the user lie within the optimum bedtime window, in this example 22:00-23:00. In such example, a feedback such as "You have gone to bed in the correct time during the past 7 days. Maintaining a consistent sleep schedule helps you in getting quality sleep night after night." may be provided to the user. As shown in FIG. 5B, the bedtime of the user does not lie within the optimum bedtime window, in this example 22:00-23:00 In such example, a feedback such as "You have gone to bed a bit too late during the past days. Try to maintain a consistent sleep schedule, it will help you in getting quality sleep night after night." may be provided to the user.

Figure 6:
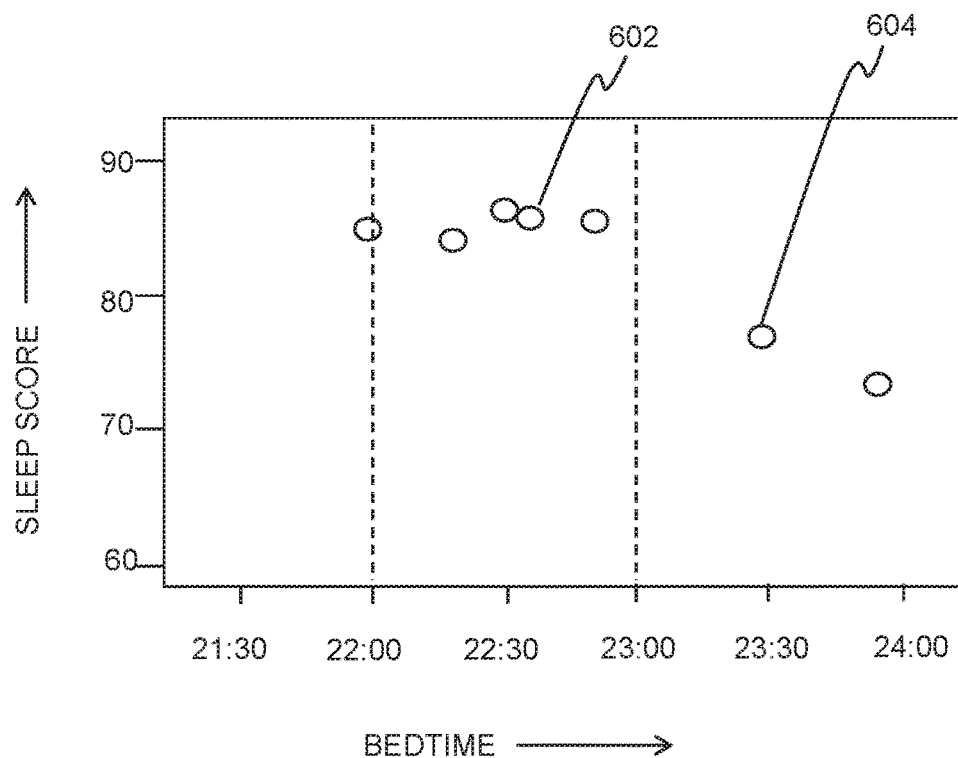
FIG. 6 is an illustration of feedback associated with the sleep scores aligned with the bedtimes of the user determined over a predefined number of days, in accordance with an exemplary embodiment of the present disclosure.

Referring to FIG. 6, there is shown an illustration of feedback associated with the sleep scores aligned with the bedtimes of the user determined over a predefined number of days, in accordance with an exemplary embodiment of the present disclosure. The processing module determines the moment of falling asleep and calculates the sleep scores associated with the bedtime of the user, as explained above. Subsequently, the user is given feedback depending upon the calculated sleep scores corresponding to the bedtime. As shown, a first bedtime 602 of the user lies within the optimum bedtime window, wherein the optimum bedtime window is between 22:00 and 23:00. Subsequently, the sleep score of the user at the first bedtime 602 is high. Furthermore, sleep score of bedtimes in the optimum bedtime window are high. Subsequently, a feedback such as "You went to bed on optimal time" may be provided to the user when the bedtime is in the optimum bedtime window. In another instance, the bedtimes of the user do not lie within the optimum-bedtime window, such as at a second bedtime 604. Subsequently, the sleep score of the user is low. In such instance, a feedback such as "You went to bed a bit too late" may be provided to the user.

Figure 7:
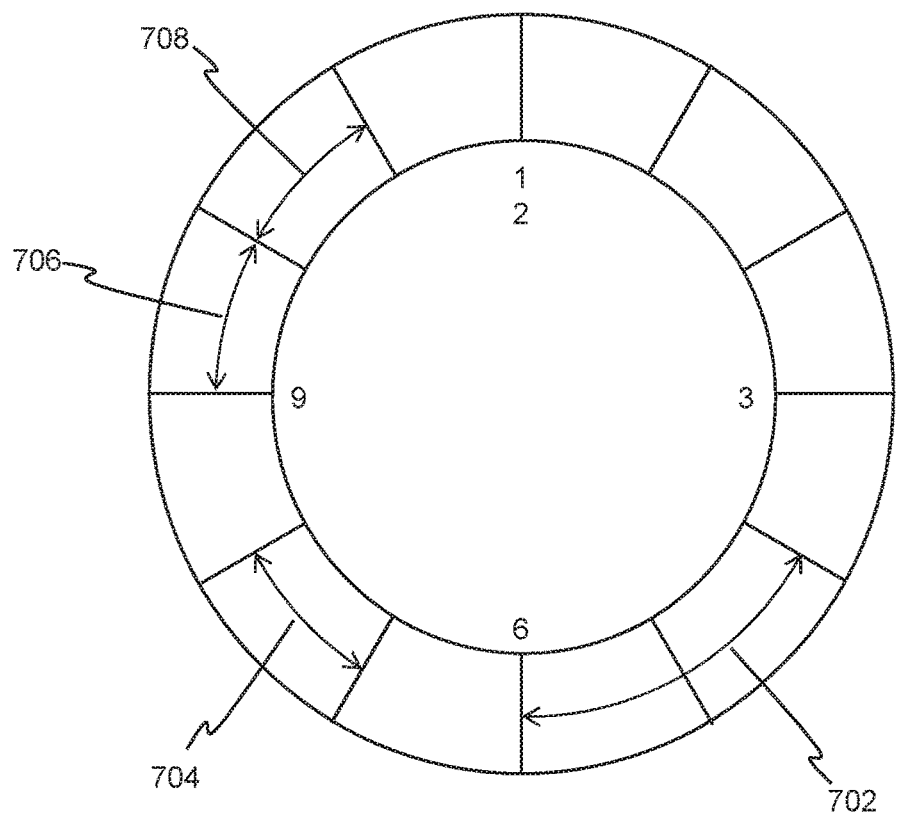
FIG. 7 is an illustration of guiding program for a user, in accordance with an exemplary embodiment of the present disclosure.

Referring to FIG. 7, there is shown an illustration of a guiding program for a user, in accordance with an exemplary embodiment of the present disclosure. As shown, in a first time period 702, the user is advised to perform light exercise owing to lack of physical activity throughout the day. In an example, the first time period 702 for the light exercise may be 6:00 pm to 7:00 pm. Furthermore, in a second time period 704, the user may be advised to have light meal. In such example, the second time period 704 for the light meal may be 7:00 pm to 8:00 pm. Moreover, in a third time period 706, the user is advised to wind down the activities to avoid any further stress. In such example, the third time period 706 for winding down may be between 9:00 pm to 10:00 pm. Furthermore, the user is further advised to go to the bed in the optimum bedtime window 708. In such example, the optimum bedtime window may be 10:00 pm to 11:00 pm.

Figure 8:
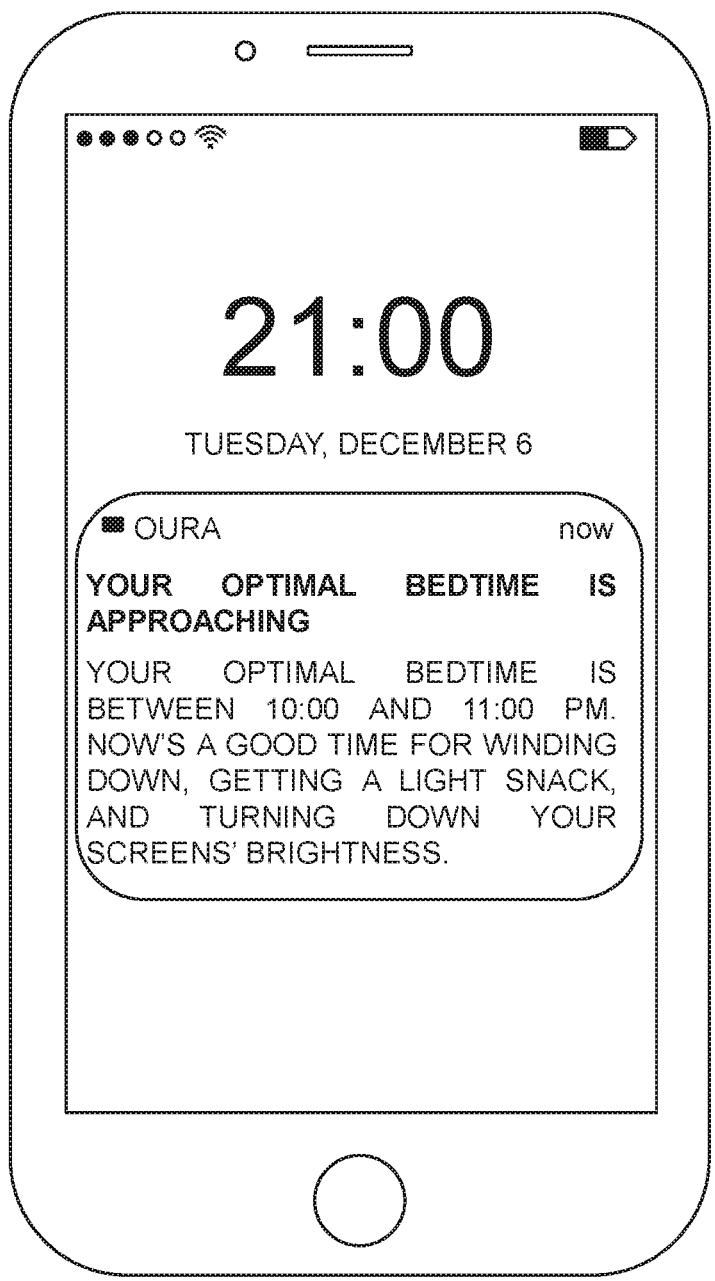
FIG. 8 is a schematic illustration of feedback notification provided on the mobile communication device, in accordance with an exemplary embodiment of the present disclosure

Referring to FIG. 8, there is shown a schematic illustration of feedback notification provided on the mobile communication device, in accordance with an exemplary embodiment of the present disclosure. In this example, a feedback such as "Your optimal bedtime is approaching. Your optimal bedtime is between 10:00 and 11:00 PM. Now it is a good time for winding down, getting a light snack, and turning down your screen brightness" can be provided to the user.

Figure 9:
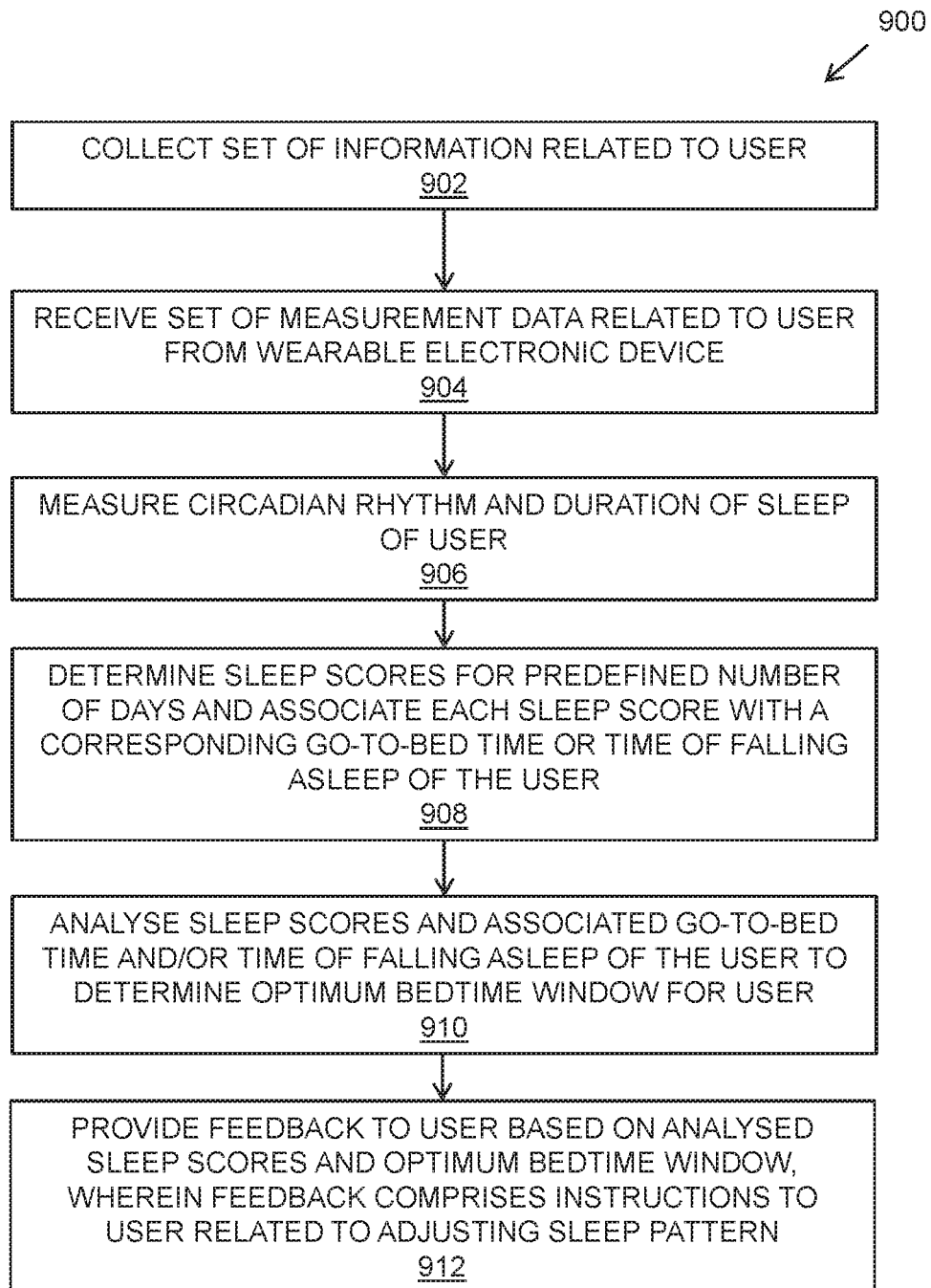
FIG. 9 is an illustration of steps of a method for providing feedback to a user for adjusting sleep pattern of the user, in accordance with an embodiment of the present disclosure.

Referring to FIG. 9, illustrated are steps of a method 900 for providing feedback to a user for adjusting sleep pattern of the user, in accordance with an embodiment of the present disclosure. At a step 902, a set of information related to the user is collected. At a step 904, a set of measurement data related to the user from a wearable electronic device is received. At a step 906, circadian rhythm and duration of sleep of the user are measured. At a step 908, sleep scores for a predefined number of days are determined. A sleep score is determined for each of the predefined number of days from the collected set of information, the set of measurement data, the circadian rhythm and the duration of sleep of the user. At a step 910, the sleep scores are analysed to determine an optimum bedtime window for the user. At a step 912, feedback based on the analysed sleep scores and the optimum bedtime window is provided to the user.

The steps 902 to 912 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for sleep monitoring, the method comprising:
receiving a set of measurement data related to a user from a wearable electronic device;
determining a sleep score for at least one day from the set of measurement data, a circadian rhythm of the user, and a duration of sleep of the user, wherein the sleep score corresponds to a time of falling asleep of the user;
providing, to the user and based at least in part on analysing the sleep score and the time of falling asleep of the user to determine an optimum bedtime window for the user, instructions comprising a first go-to-bed time corresponding to a first night; and
determining a second go-to-bed time corresponding to a second night based at least in part on the first go-to-bed time, the second go-to-bed time between the first go-to-bed time and the optimum bedtime window.

2. The method of claim 1, wherein providing the instructions further comprises:
providing, to the user, second instructions comprising the second go-to-bed time corresponding to the second night.

3. The method of claim 1, wherein providing the instructions is based at least in part on a second set of measurement data for a consecutive day, wherein the consecutive day is succeeded by the at least one day.

4. The method of claim 1, wherein the duration of sleep is measured as a first time between a first moment of falling to sleep and a second moment of waking up or as a second time between a third moment of going to bed and the second moment of waking up, wherein the first moment, the second moment, and the third moment are determined based on at least one of a change in heart rate, a change in body or skin temperature, or a change in movement of the user.

5. The method of claim 1, further comprising:
collecting a set of information related to the user, wherein the set of information comprises physiological performance related information based on an external data input by the user.

6. The method of claim 5, wherein the sleep score is determined based at least in part on the set of information.

7. The method of claim 5, wherein the external data input comprises at least one of travel information, time zone, calendar, working schedule and holidays.

8. The method of claim 1, further comprising:
storing a set of parameters related to sleep patterns.

9. An apparatus for sleep monitoring, comprising:
a processor;
memory coupled with the processor; and
first instructions stored in the memory and executable by the processor to cause the apparatus to:
receive a set of measurement data related to a user from a wearable electronic device;
determine a sleep score for at least one day from the set of measurement data, a circadian rhythm of the user, and a duration of sleep of the user, wherein the sleep score corresponds to a time of falling asleep of the user;
provide, to the user and based at least in part on analysing the sleep score and the time of falling asleep of the user to determine an optimum bedtime window for the user, second instructions comprising a first go-to-bed time corresponding to a first night; and
determine a second go-to-bed time corresponding to a second night based at least in part on the first go-to-bed time, the second go-to-bed time between the first go-to-bed time and the optimum bedtime window.

10. The apparatus of claim 9, wherein the first instructions are further executable by the processor to cause the apparatus to:
provide, to the user, third instructions comprising the second go-to-bed time corresponding to the second night.

11. The apparatus of claim 9, wherein providing the second instructions is based at least in part on a second set of measurement data for a consecutive day, wherein the consecutive day is succeeded by the at least one day.

12. The apparatus of claim 9, wherein the duration of sleep is measured as a first time between a first moment of falling to sleep and a second moment of waking up or as a second time between a third moment of going to bed and the second moment of waking up, wherein the first moment, the second moment, and the third moment are determined based on at least one of a change in heart rate, a change in body or skin temperature, and a change in movement of the user.

13. The apparatus of claim 9, wherein the first instructions are further executable by the processor to cause the apparatus to:
collect a set of information related to the user, wherein the set of information comprises physiological performance related information based on an external data input by the user.

14. The apparatus of claim 13, wherein the sleep score is determined based at least in part on the set of information.

15. The apparatus of claim 13, wherein the external data input comprises at least one of travel information, time zone, calendar, working schedule and holidays.

16. The apparatus of claim 9, wherein the first instructions are further executable by the processor to cause the apparatus to:
store a set of parameters related to sleep patterns.

17. A system for sleep monitoring, the system comprising:
a wearable electronic device configured to be worn by a user;
a mobile communication device configured to communicate with the wearable electronic device; and
a processing module configured to communicate with at least one of the mobile communication device or the wearable electronic device, the processing module operable to:
receive a set of measurement data related to the user from the wearable electronic device;
determine a sleep score for at least one day from the set of measurement data, a circadian rhythm of the user, and a duration of sleep of the user, wherein the sleep score corresponds to a time of falling asleep of the user;
provide, to the user and based at least in part on analysing the sleep score and the time of falling asleep of the user to determine an optimum bedtime window for the user, instructions comprising a first go-to-bed time corresponding to a first night; and
determine a second go-to-bed time corresponding to a second night based at least in part on the first go-to-bed time, the second go-to-bed time between the first go-to-bed time and the optimum bedtime window.

18. The system of claim 17, wherein the wearable electronic device is operable to measure a second set of measurement data for a consecutive day, wherein the consecutive day is succeeded by the at least one day and the processing module is operable to provide the instructions based at least in part on the second set of measurement data for the consecutive day.

19. The system of claim 17, wherein the processing module is operable to store a set of parameters related to sleep patterns.

20. The system of claim 17, wherein the mobile communication device or the wearable electronic device comprises the processing module.

* * * * *